United States Patent [19]

Harding, Jr.

[11] Patent Number: 4,654,080
[45] Date of Patent: Mar. 31, 1987

[54] RODENT REPELLENT PAINT AND BARS

[76] Inventor: Norman T. Harding, Jr., 2320 Laketon Rd., Pittsburgh, Pa. 15221

[21] Appl. No.: 745,356

[22] Filed: Jun. 14, 1985

[51] Int. Cl.$^4$ .................................................. C09D 5/14
[52] U.S. Cl. ............................... 106/15.05; 106/18.29; 106/74; 106/270
[58] Field of Search .................... 106/15.05, 18.29, 74, 106/270; 424/30

[56] References Cited

U.S. PATENT DOCUMENTS

| | | | |
|---|---|---|---|
| 75,561 | 3/1868 | McKinsey | 424/195.1 |
| 136,185 | 2/1873 | Sears | 424/195.1 |
| 779,634 | 1/1905 | Allen | 424/161 |
| 1,506,575 | 8/1924 | Eberhardt | 424/195.1 |
| 1,871,949 | 8/1932 | Bottrell | 514/711 |
| 2,159,550 | 5/1939 | Cross | 424/195.1 |
| 4,378,374 | 3/1983 | Reggio et al. | 426/3 |

OTHER PUBLICATIONS

Pest Control With Nature's Chemicals by Elroy L. Rice, cover, title page and pp. 16, 17, 186 and 187, Jul. 30, 1985.

Primary Examiner—Lorenzo B. Hayes
Attorney, Agent, or Firm—Buell, Zieseneheim, Beck & Alstadt

[57] ABSTRACT

Rodent repellent paints and solid are disclosed which are comprised of thujone oil or cedar leaf oil in a suitable carrier such as lacquer, sodium silicate or paraffin.

4 Claims, No Drawings

4,654,080

RODENT REPELLENT PAINT AND BARS

FIELD OF INVENTION

The present invention relates to a paint and a paraffin based solid having rodent repellent characteristics.

DESCRIPTION OF THE PRIOR ART

For many years numerous attempts have been made to keep rats and mice away from homes, storage bins and other areas. Most commonly, traps or poisons are used to kill the vermin. In addition to creating dead animal disposal problems, traps and poisons also pose dangers to children, pets and animals. Furthermore, traps and poisons must be monitored. Sprung traps must be reset and consumed poison must be replaced. Also, many people have found that for each rat they kill with traps or poison there are others in the area who survive.

Rather than try to kill the rodents which are present, a better approach is to deter them from entering the area. Certain plant extracts have been found to have repellent properties. Bottrell in U.S. Pat. No. 1,871,949 uses oil of peppermint to repell rodents. Cross in U.S. Pat. No. 2,159,550 teaches that extracts from the wood and fruit of the Areca catechu plant have repellent properties. Yet, neither of these materials have had any commercial success.

The art has also recognized that certain plants repel rodents. For example, pieces of the wormwood plant (Artemsia Absinthium) have been used as moth and rodent repellents. But, these pieces are only effective for a relatively short period of time, typically a few days.

The art has generally attributed the repellent charactersitics of the wormwood and other plants to the presence of alkyloids in the plant. Apparently, these alkyloids are poisonous. However, I have discovered that thujone oil, a natural oil of the wormwood plant, or cedar leaf oil from the cedar tree, not alkyloids, will repel rodents when used in the manner here described.

SUMMARY OF THE INVENTION

I provide a rodent repellent in either liquid or solid form by combining thujone oil or cedar leaf oil with a suitable liquid or solid carrier such as lacquer or paraffin.

I prefer to use from one to six parts thujone oil for each eight parts paraffin to form a repellent bar.

I also prefer to use a paint comprised of thujone oil and lacquer in a mixture having 25% to 40% thujone oil.

I also prefer to combine thujone oil and sodium silicate in a ratio of 3 parts thujone oil for each 22 parts sodium silicate.

DESCRIPTION OF THE PREFERRED EMBODIMENTS

I have found that certain compositions of thujone oil or cedar leaf oil and either a liquid or solid carrier will repell rodents for a significant period of time. A combination of thujone oil or cedar leaf oil and lacquer when used like a paint will keep rodents away from the painted area for between three and five years. When these oils are combined with paraffin the product can be used like mothballs. The effective life of the product usually is six months to a year depending on the environment.

To make these products, I first extract the oil from the plant source. Thujone oil is extracted from the wormwood plant and cedar leaf oil is obtained from the cedar tree. Thujone oil is also commercially available as it is used in perfume. Both oils have a similar aroma and can be used interchangeably. Then the oil is combined with a suitable carrier to form a repellent paint or solid.

A. The repellent paint

I have found that lacquer is a suitable carrier for thujone oil and cedar leaf oil. The oil and lacquer are combined so that at least 25% of the mixture is oil. Then, the combination is applied to a surface like any standard paint. If the lacquer does not contain aromatic hydrocarbons, I have found that a ratio in excess of 31% oil clouds the lacquer and makes it unsuitable. Lacquers which contain aromatic hydrocarbons require more oil to be effective. For such lacquers one must use at least,. 40% oil.

Another suitable carrier is sodium silicate. I prefer to combine 12% oil and 88% sodium silicate to form a paint. However, any combination containing from 4% to 25% oil will be effective.

I have conducted several experiments to show the effectiveness of my rat and mice repellents. The first experiment consisted of three boxes with the entrances to each blocked with sheets of screen. The rats were placed in the middle box. The box on the left contained food and the walls of the box were stained with the rat and mice repellent. This repellent was a mixture of 12% thujone oil and 88% lacquer. The box on the right contained only food and the walls were not stained. At the end of five days, the metal screens were lifted. The rats would not enter the box with the rat and mice repellent, but ate from the box that contained no repellent.

In a second experiment, I used two boxes separated by a metal screen. A neutral box without repellent on the walls housed the rats. The remaining box contained the rate and mice repellent and contained the food. After five days the metal screen which separated the boxes was lifted. The rats would not enter the box stained with the rat and mice repellent to get the food. The repellent used in this experiment was a mixture of 12% thujone oil and 88% lacquer.

B. The repellent solid

I have also found that a solid rodent repellent can be made by mixing thujone oil or cedar leaf oil with paraffin and molding the mixture to a desired shape, preferably a bar. I have found that a mixture of from 6% to 42% oil is effective. Compounds of from 1 to 6 parts oil of thujone for each 8 parts paraffin were particularly useful.

Experiments with a solid repellent having 6% thujone oil and 94% paraffin demonstrated the effectiveness of my repellant bars.

While I have described certain present preferred embodiments of my invention it should be distinctly understood that the invention is not limited thereto but may be variously embodied within the scope of the following claims.

I claim:

1. A rodent repellent paint comprised of 22% to 31% oil of thujone, and 69% to 88% sodium silicate.

2. A rodent repellent paint comprised of 12% thujone oil and 88% sodium silicate.

3. A rodent repellent comprised of paraffin and thujone oil wherein there are from 1 to 6 parts oil for each 8 parts paraffin.

4. A rodent repellent comprised of 6% thujone oil and 94% paraffin.

* * * * *

UNITED STATES PATENT AND TRADEMARK OFFICE
CERTIFICATE OF CORRECTION

PATENT NO. : 4,654,080

DATED : March 31, 1987.

INVENTOR(S) : NORMAN T. HARDING, JR.

It is certified that error appears in the above-identified patent and that said Letters Patent is hereby corrected as shown below:

Column 2, line 16, after least, delete ",."

Signed and Sealed this

Twenty-third Day of June, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,654,080

DATED : March 31, 1987

INVENTOR(S) : NORMAN T. HARDING, JR.

It is certified that error appears in the above-identified patent and that said Letters Patent is hereby corrected as shown below:

Column 2, line 35, change "rate" to --rat--.

Signed and Sealed this

Twenty-eighth Day of July, 1987

*Attest:*

DONALD J. QUIGG

*Attesting Officer*  *Commissioner of Patents and Trademarks*